US010811130B2

(12) United States Patent
Cronin et al.

(10) Patent No.: US 10,811,130 B2
(45) Date of Patent: Oct. 20, 2020

(54) PULSE OXIMETER INTEGRATION FOR EVALUATING AND UPDATING A DRUG ADMINISTRATION SCHEDULE USING EFFECTIVENESS RATING

(71) Applicant: KONINKLIJKE PHILIPS N.V., Eindhoven (NL)

(72) Inventors: John Cronin, Bonita Springs, FL (US); Steven Matthew Philbin, Bonita Springs, FL (US)

(73) Assignee: Koninklijke Philips N.V., Eindhoven (NL)

( * ) Notice: Subject to any disclaimer, the term of this patent is extended or adjusted under 35 U.S.C. 154(b) by 288 days.

(21) Appl. No.: 15/776,123

(22) PCT Filed: Nov. 21, 2016

(86) PCT No.: PCT/EP2016/078354
§ 371 (c)(1),
(2) Date: May 15, 2018

(87) PCT Pub. No.: WO2017/089317
PCT Pub. Date: Jun. 1, 2017

(65) Prior Publication Data
US 2018/0336962 A1 Nov. 22, 2018

Related U.S. Application Data

(60) Provisional application No. 62/259,049, filed on Nov. 23, 2015.

(30) Foreign Application Priority Data

Mar. 4, 2016 (EP) .................................... 16158623

(51) Int. Cl.
*G16H 20/17* (2018.01)
*G16H 50/30* (2018.01)
(Continued)

(52) U.S. Cl.
CPC ......... *G16H 20/17* (2018.01); *A61B 5/14552* (2013.01); *A61B 5/4839* (2013.01);
(Continued)

(58) Field of Classification Search
CPC ........ G16H 20/17; G16H 10/60; G16H 50/30; G16H 40/63; A61B 5/14552; A61B 5/4839; A61B 5/4848; A61B 5/742
(Continued)

(56) References Cited

U.S. PATENT DOCUMENTS 5,298,021 A   3/1994 Sherer
5,378,231 A   1/1995 Johnson
(Continued)

FOREIGN PATENT DOCUMENTS

JP   2001052056 A   2/2001
JP   2007007135 A   1/2007
(Continued)

OTHER PUBLICATIONS

Tim Vanderveen, "From Smart Pumps to Intelligent Infusion Systems—The Promise of Interoperability"; May 27, 2014; http://psqh.com/mayjune2014/fromsmartpumpstointelligentinfusionsystemstheprom iseofinteroperability.
(Continued)

*Primary Examiner* — Joy Chng (57) ABSTRACT

Method of scheduling drug administration using a pulse-oximetry integrated intravenous fluid system comprising retrieving from at least one network server database via an intravenous pump unit patient-related and drug-related data and information. The retrieved data are displayed on the intravenous pump unit interface and then a patient's pulse oximetry data is acquired. Using the pulse oximetry data, patient history, patient condition, diagnosis, and information relating to the one or more drugs, a medical personnel
(Continued)

determines a schedule of drug administration. During the set duration of a drug administration schedule, one or more observed effects of the one or more drugs administered to the patient via the intravenous pump unit interface is inputted into the IV pump unit, and the patient record stored in the at least one network database is updated.

15 Claims, 5 Drawing Sheets

(51) Int. Cl.
  *G16H 10/60* (2018.01)
  *G16H 40/63* (2018.01)
  *A61B 5/1455* (2006.01)
  *A61B 5/00* (2006.01)

(52) U.S. Cl.
  CPC ............ *A61B 5/4848* (2013.01); *A61B 5/742* (2013.01); *G16H 10/60* (2018.01); *G16H 40/63* (2018.01); *G16H 50/30* (2018.01)

(58) Field of Classification Search
  USPC .......................................................... 705/2–3
  See application file for complete search history.

(56) References Cited

U.S. PATENT DOCUMENTS

| | | | |
|---|---|---|---|
| 7,657,443 B2 | 2/2010 | Crass et al. | |
| 7,860,583 B2 | 12/2010 | Condurso | |
| 8,645,154 B2 | 2/2014 | Eggers | |
| 2003/0051737 A1 | 3/2003 | Hickle | |
| 2003/0106553 A1 | 6/2003 | Vanderveen | |
| 2003/0145854 A1* | 8/2003 | Hickle | A61M 5/142 128/204.18 |
| 2006/0042632 A1* | 3/2006 | Bishop | A61B 5/0836 128/207.18 |
| 2006/0047538 A1* | 3/2006 | Condurso | G06F 19/3456 705/3 |
| 2008/0114211 A1 | 5/2008 | Karst | |
| 2010/0030089 A1* | 2/2010 | Hyde | G06F 19/3481 600/508 |
| 2010/0268157 A1 | 10/2010 | Wehba | |
| 2011/0082440 A1* | 4/2011 | Kimmo | A61M 5/168 604/503 |
| 2011/0313789 A1 | 12/2011 | Kamen | |
| 2012/0084101 A1 | 4/2012 | Qadri | |
| 2012/0191060 A1 | 7/2012 | Banister | |

FOREIGN PATENT DOCUMENTS

| | | |
|---|---|---|
| WO | 2005/056087 | 6/2005 |
| WO | 2011/075687 | 6/2011 |

OTHER PUBLICATIONS

Grossmann, et al., "Securely control infusion pumps via internet for efficient remote therapy of pain"; IFMBE Proceedings vol. 14/1; Jul. 5, 2007.

Krishnan, et al., "Design of Interoperability-Coupled Safe Infusion Therapy in a Telemetry Setting"; IFMBE Proceedings 24, May 20, 2009.

Tanaka, K. et al., "Circadian chronotherapy for metastatic liver tumor". Nippon rinsho, Japanese Journal of Clinical Medicine 71(12):2158-64.

* cited by examiner

FIG. 1

Doctor GUI

| Height: | 5'10" | → |
| Weight: | 170 lbs. | → |
| Age: | 20 | → |
| Gender: | Male | → |
| Body Fat Percentage: | 15% | → |
| Ethnicity: | Caucasian | → |
| Current Condition: | Alcohol Poisoning | → |
| Medication: | IV Fluids | → |

202
208

Enter Medical History — 204

Save — 206

Medical History GUI

Has the Patient had any of the following:

| AIDS/HIV: | [ ] |
| Alcoholism: | [X] |
| Anemia: | [ ] |
| Anorexia: | [ ] |
| Asthma: | [X] |
| Bleeding Disorders: | [ ] |
| Cancer: | [ ] |

← →

214
212

Save — 216

Effectiveness GUI

On a scale of 1-10, rate the overall effectiveness of the treatment

10  →

220

Save — 222

PULSE OXIMETER INTEGRATION FOR EVALUATING AND UPDATING A DRUG ADMINISTRATION SCHEDULE USING EFFECTIVENESS RATING

CROSS REFERENCE TO RELATED APPLICATIONS

This application is the U.S. National Phase application under 35 U.S.C. § 371 of International Application No. PCT/EP2016/078354, filed Nov. 21, 2016, published as WO 2017/089317 on Jun. 1, 2017, which claims the benefit of European Patent Application Number 16158623.5 filed Mar. 4, 2016 and U.S. Provisional Patent Application No. 62/259,049 filed Nov. 23, 2015. These applications are hereby incorporated by reference herein.

BACKGROUND OF THE INVENTION

The timing of drug administration can substantially affect drug efficacy and thus impact treatment or testing protocols, such as diagnostic laboratory testing. For example, if a physician is using the measured quantity of drug in a patient's blood to determine the drug dosing to be used for the patient, any dosing recommendation by the physician could be significantly influenced by the timing of the drug administration. In addition, many drugs have to be administered at specific times in relation to meals to achieve the drugs' optimal efficacy.

Drug administration timing could also impact drug efficacy in another way. For example, certain drugs are known to target circadian genes. A study reported that 56% of the 100 best-selling drugs in the U.S. target the product of a circadian gene. This means these drugs' efficacy could be impacted by the drug administration timing because of the patient's biological clock. Diseases that have been found to be most closely associated with circadian genes include Type 2 diabetes, cancer, obesity, Alzheimer's disease, schizophrenia, Down syndrome, and coronary artery disease.

Treatment protocols that are partly designed to take into account the influence of drug administration timing on drug efficacy have already proved to be influential owing to the valuable insights provided by what we now know about the timing effect on the efficacy of many drugs. For example, we now know that short half-life statins are most effective when taken before bedtime because our body manufactures cholesterol while we sleep. Also, we now know that aspirin should be taken at night when used for preventing heart attacks.

US 2003/0106553 discloses a method for controlling patient self-administration of fluid infusions comprising monitoring patient conditions by connecting a capnography unit to the patient, a user interface adapted to provide an interface with a user, inputting patient condition limits into the interface unit, comparing monitored patient conditions to patient condition limits in the interface and generating a signal indicative of the comparison, and connecting the patient to an infusion unit, which communicates with the interface unit. US 2011/0313789 discloses a method whereby a physician can order the dose of medication, either directly or by accepting a default standard starting dose provided by a monitoring system. The physician may specify the maximum fluid infusion rate for the infusion pump to assist the pharmacist in preparing the proper concentration of the drug in a bag for infusion.

U.S. Pat. No. 5,298,021 discloses an infusion pump system that allows various inputs that include patient data inputs provided to a controller via certain medical instruments attached to the patient, each of which provide particular physiological data to the controller. U.S. Pat. No. 7,860,583 discloses adjusting the therapy delivered to the patient depending on the outcome of the comparison by providing control signals to medical devices tasked with delivery of the therapy to the patient.

US 2006/0047538 A1 discloses a system and method of managing therapy provided to patients in an institution. The system monitors all aspects of the medication delivery to a patient, as well as other information related to the patient, such as values of vital signs, laboratory results and patient factors such as history, diagnosis, allergies and the like. The system includes one or more databases of information, including institutionally developed rules, guidelines and protocol representing the best medical practices of the institution. The system provides alerts and/or recommendations based on the application of the rules to the information being monitored, and alerts care givers accordingly, providing for dynamic adjustment of the patient's therapy. The system also monitors the status of the alerts, and if no action is taken in a selected period of time, may escalate the priority of the alert and/or halt the delivery of medication to the patient until the alert is resolved.

SUMMARY OF THE INVENTION

According to aspects of the present invention a method and system of scheduling drug administration using a pulse-oximetry integrated intravenous fluid system as well as a non-transitory computer-readable storage medium are presented as defined in the independent claims.

The present invention relates to a method of scheduling drug administration using a pulse-oximetry integrated intravenous fluid system comprising retrieving from a network database via an intravenous pump unit patient-related and drug-related data and information that include patient history, patient condition, diagnosis, and information relating to the one or more drugs to be administered to the patient, wherein the retrieved patient data are displayed on the intravenous pump unit interface. Pulse oximetry data are then acquired from a patient, including any other desired medical or physiological parameter data. The retrieved patient-related information, drug-related data information, and the acquired pulse oximetry data, plus any additional acquired medical or physiological parameter data are used to determine a schedule of drug administration. After one or more drugs are administered during a selected drug delivery schedule, one or more observed effects of the one or more drugs administered to the patient are inputted via the intravenous pump unit interface. The patient data stored in at least one database is then updated to include the newly-acquired data and any observations, conclusions, and comments by the medical personnel monitoring the patient.

BRIEF DESCRIPTION OF THE DRAWINGS

The accompanying drawings, which are included to provide a further understanding of the invention, are incorporated herein to illustrate various embodiments of the invention. Along with the description, they also serve to explain the principle of the invention. In the drawings.

DETAILED DESCRIPTION OF THE EMBODIMENTS

The following are definitions of terms as used in the various embodiments of the present invention.

The term "database" as used herein refers to a collection of data and information organized in such a way as to allow the data and information to be stored, retrieved, updated, and manipulated and to allow them to be presented into one or more formats such as in table form or to be grouped into text, numbers, images, and audio data. The database typically resides in computer memory that includes various types of volatile and non-volatile computer memory. "Database" as used herein also refers to conventional databases that may reside locally or that may be accessed from a remote location, e.g., remote network servers. The term "database" as used herein may also refer to a segment or portion of a larger database, which in this case forms a type of database within a database. Memory wherein the database resides may include high-speed random access memory or non-volatile memory such as magnetic disk storage devices, optical storage devices, and flash memory. Memory where the database resides may also comprise one or more software for processing and organizing data received by and stored into the database.

The term "analyzing" as used herein collectively refers to analyzing, retrieving, displaying, processing, and comparing, including verifying or confirming the accuracy or correctness of data such as a patient's health-related data.

The term "effectiveness" as used herein refers to drug efficacy when the term "effectiveness" is used in relation to a drug's ability to improve a patient's medical condition. The term "effectiveness" also refers to the extent to which a process, procedure, or system, such as a particular drug administration schedule, leads to an improvement in a patient's medical condition.

The term "measurement mode" as used herein refers to data or information that includes the type of measurement performed by a medical device, an identifier of the medical device used to acquire the health-related data, including one or more specific medical device parameters that were measured using the medical device. A measurement mode also includes one or more measurement schedules defined or set, either manually or automatically, according to one or more measurement or monitoring protocols for acquiring health-related data by the medical device. For example, a patient diagnosed with fever is asked to take an analgesic when the patient's measured temperature reaches 38° C. or higher. A temperature monitoring system will take the patient's temperature readings every 30 minutes until the fever has subsided. The programmed schedules will typically vary depending on the patient's needs and the severity of the monitored disease.

The term "medical parameter" as used herein refers to a quantity, parameter, variable, or data that a medical device or sensor detects, measures, acquires, processes, analyzes, or transmits to another device.

The present invention relates to a method of scheduling drug administration using a pulse-oximetry integrated intravenous fluid system comprising: retrieving from a patients database via an intravenous pump unit patient data comprising patient data and information that includes patient history, family history, any pre-existing disease, known allergies, present patient condition, diagnosis, and information relating to the one or more drugs to be administered to the patient; displaying the retrieved patient data on the intravenous pump unit interface; acquiring pulse oximetry data from a patient; using the pulse oximetry data, patient history, patient condition, diagnosis, and information relating to the one or more drugs to determine a schedule of drug administration; inputting one or more observed effects of the one or more drugs administered to the patient via the intravenous (IV) pump unit interface after administering the at least one drug; and updating the patient data stored in at least one database.

The various data and information relating to patient history, condition, diagnosis, and known drug-related information—such as pharmacokinetics, bioavailability, recommended dosage, known side-effects, and contraindications—are used preferably along with one or more measurement modes to determine a schedule of drug administration. The one or more measurement modes includes the type of measurement performed by a medical device, an identifier of the medical device used to acquire the health-related data, including one or more specific medical device parameters that were measured using the medical device. A measurement mode also includes one or more medical parameter measurement schedules defined or set, either manually or automatically, according to one or more measurement or monitoring protocols for acquiring health-related data by at least one medical device attached to the IV pump unit. The patient-related and drug-related information and data are entered into the IV pump unit either manually or automatically uploaded into the IV pump unit from one or more network servers connected to the pump unit.

In one embodiment of the present invention, the IV pump unit accesses either wirelessly or via wired connections one or more network server databases via the internet to cloud/retrieve and downloads patient and drug-related data and information into the IV pump unit for use in determining the best drug delivery schedule for the patient. The IV pump unit preferably comprises an intravenous drug delivery system for administering one or more drugs to a patient, a controller for controlling the delivery of one or more drugs as part of a patient treatment protocol, one or more displays, graphical unit interface, at least one software for processing, scheduling drug delivery, and controlling and monitoring drug delivery, an operating system, one or more processors, one or more input devices such as a keyboard or mouse, one or more memory modules for storing data, wireless or wired connectivity to other devices and to the cloud/internet.

In one preferred embodiment of the present invention, one or more IV pump lines are connected to a patient. The use of multiple IV lines is particularly useful in situations where a patient has to be treated with more than one drug at different time intervals, such as when simultaneous drug administration of two or more drugs is to be avoided to minimize any adverse drug interactions involving the two or more drugs to be administered, or when the optimum drug delivery schedules for the separate drugs are different, e.g., one drug needs to be scheduled for administration early in the morning, while the other drug needs to be administered right before the patient's scheduled bedtime. This embodiment is also preferable particularly when the two or more drugs that need to be administered to the patient have different solubility in different drug carriers or solvents, e.g., one drug may be water-soluble while the other drug may be oil-soluble thus necessitating the use of at least two different solvents or solutions as drug carrier and at least two different IV lines. In a preferred embodiment, one main IV line may be connected to one or more IV lines. This embodiment is useful in cases where the drugs administered through the connected IV lines have the same or similar solubility in the same solvent or solution, and the two or more drugs from the separate lines need to be administered to the patient either simultaneously at once or over a period of time. Having a single main IV line that is also connected to one or more additional IV lines is particularly advantageous in that it allows the administration of more than one drug using only one main IV line connected to the patient directly.

Multiple IV lines may be necessary in cases where various routes of administration are required for a particular patient. Various examples of the different administration routes that may be used according to the present invention includes intra-arterial (into an artery for use with, for example, vasodilator drugs in the treatment of vasospasm and thrombolytic drugs for treatment of embolism); epicutaneous or topical (application onto the skin, can be used for typical local anesthesia), intradermal, (into the skin itself, e.g., for tuberculosis testing); intramuscular (into a muscle, used with many vaccines, antibiotics, and long-term psychoactive agents); intraperitoneal, (infusion or injection into the peritoneum, e.g., peritoneal dialysis; intrathecal (into the spinal canal, most commonly used for spinal anesthesia and chemotherapy); intrauterine; intravenous (into a vein, can be used with many drugs, total parenteral nutrition); intravesical infusion (into the urinary bladder); and subcutaneous (under the skin, e.g., insulin administration).

Preferably, the IV pump unit is capable of varying the flow rate used to administer the drug depending on, for example, how the patient reacts to the drug. This is particularly useful in cases where the patient is being administered a particular drug or class of drugs for the first time, so it is unclear at the outset how the patient is going to respond to the drug. The flow or drug delivery rate is also preferably varied to enhance the efficacy of the at least one drug being administered to the patient by taking the flow rate into account—along with other parameters such as known optimal dosage for a patient of a certain age, gender, weight, and ethnic origin—when determining a drug administration schedule for a patient. For example, a treatment protocol may be designed such that the drug administration schedule is set to gradually decrease the drug flow rates over the treatment period when the patient's condition shows signs of improvement.

In a preferred embodiment of the present invention, an authorized medical personnel performs one or more of the following steps when reviewing or determining a drug administration schedule: enter patient's name/account number; compare drug order to patient profile in detail; enter drug; verify dose; indicate whether drug should be administered with full stomach or empty stomach and whether substitution allowed or not allowed; enter prescriber name; view previous pulse oximetry data; view recorded patient response to administered drug over a period of time, e.g., patient condition is improving during the treatment period or patient experiencing one or more side-effects; modify drug administration schedule based on reviewed data and information; enter revised drug administration schedule; and enter any comments or recommendations in clinical comments field.

The medical personnel analyzes the acquired data preferably using the IV pump unit for one more purposes: diagnose a patient condition, determine any signs of improvement in the patient's condition, detect any anomalous feature in the viewed data for any sign of abnormality or disease, determine if a prescribed treatment is working, determine if a drug dosage or mode of administration should be changed, determine if the patient should be referred to one or more specialists, determine whether a treatment should be terminated, and determine if the current drug delivery schedule should be changed. When the medical personnel has completed the patient data analysis, the acquired raw and processed data including patient and drug-related information, as well as data measured by one or more medical devices or sensors—are preferably initially stored in the IV pump unit's memory. Optionally, the acquired data are subsequently transmitted to and stored in one or more of the hospital network's databases.

Preferably, the attending medical personnel also inputs into the IV pump unit via the pump unit's interface the instructions for the drug administration that includes administration directions ("take," "insert," "apply"); number of units constituting one dose/dosage form; route of administration; frequency; duration if applicable ("for 5 days," "until finished"); indication if applicable (e.g., "for infection" or "for blood pressure").

In a preferred embodiment of the present invention, the drug administration schedule is determined based on one or more parameters that include drug tolerance and resistance, age, body size, routes of drug administration, gender, known allergies, family history, patient's known reaction to certain drugs, pregnancy, lactation, known genetic factors or predisposition, disease states, environmental factors, psychological factors, degree of drug ionization, a drug's lipid solubility, drug side effects, and any known drug interactions involving two or more drugs to be used in the treatment protocol. For example, if a patient is a nursing mother, drug must be administered preferably between half-an-hour to an hour after nursing or 3-4 hours before the next feed. In many cases, this permits the mother's blood to be cleared of the drug to prevent drug ingestion by the infant.

In some cases, drug administration may be performed only once, twice, or three times a day. In hospitals, standard drug administration times are generally set. These drug administration times are often fixed by hospital policy or by a drug therapy protocol. Such policies and protocols may define times for common dosing frequencies, for example, daily at 9 am, bid at 9 am and 5 pm, and every 8 hours at 6 am, 2 pm, and 10 pm. Standardized drug administration schedules are usually also determined by other factors including therapeutic issues, nursing and pharmacy efficiency, or how well services are coordinated. In addition, many hospitals and pharmacies typically have a document that medical personnel can refer to when it is unclear what the appropriate administration time is. These times are usually relayed to the medical personnel via the pharmacy's patient profile, on medication labels, and on the medication administration record.

In a preferred embodiment of the invention, the drug is administered over staggered time intervals depending on the determined optimal drug delivery schedule for the one or more drugs used in a treatment protocol. Preferably, not only is the drug administration times adjusted to achieve optimal drug delivery, but the drug flow rate and drug dosing or amount of drug delivered is also modified depending on the observed increase or decrease in the corresponding drug efficacy based on the observed patient's response to the treatment protocol.

Data relating to, for example, the patient, mode of treatment, and drug may be entered directly into the IV pump unit via its graphical unit interface by an authorized medical personnel. In one embodiment, a medical professionals logs in, after being authenticated by the IV pump unit's security protocol, various known information about the patient, drug, the mode of treatment such as the route of administration, dosing, etc. These data are then combined with acquired patient pulse oximeter data to optimize the drug delivery schedule for a patient.

In a preferred embodiment of the invention, information and data about the optimum drug delivery timing for a drug is already known. With this knowledge, an authorized personnel can simply use the known optimal drug delivery schedule for a drug to determine the actual drug delivery schedule for a patient while monitoring a patient's response to the drug, for example, every 2-3 hours over a period of 24 hours. To further refine the drug delivery timing optimization, the pulse oximeter data is preferably acquired during the monitoring period and used to modify the drug delivery schedule for the following day based on the observed patient response to the treatment protocol. For example, a scheduled drug delivery known to have maximum efficacy when administered at night is found to increase or decrease the patient's pulse rate or SpO2 level outside of the normal levels for the patient when the drug is administered at certain times such as at around 12 midnight and around 2 am. Thus, the following day's drug administration schedule is modified so the drugs are administered at times that exclude 12 midnight and 2 am.

In another embodiment, the scheduling of the drug administration is determined based on pulse oximetry data and at least one known synergistic effect between two or more drugs. In this case, the optimal drug administration schedule is designed based on the acquired pulse oximetry data, the individual known optimal drug delivery for maximum drug efficacy for each drug, and the known synergistic effects arising from the combination of the two or more drugs as part of the patient's treatment protocol. In a highly preferred embodiment of the present invention, the selected drug administration schedule is also designed to minimize any adverse side-effects from each drug or any adverse drug interactions arising from the administration of the two or more drugs, in addition to the selected drug administration schedule being also based on pulse oximetry data, the individual known optimal drug delivery for maximum drug efficacy for each drug, and the known synergistic effects arising from the combination of the two or more drugs as part of the patient's treatment protocol.

In a highly preferred embodiment of the present invention, the method for determining an optimal drug delivery schedule for a patient suffering from one or more medical conditions is used in conjunction with an automated monitoring system that allows the automated monitoring of a patient's conditions over the duration of the treatment protocol to determine the patient's response to the treatment. Thus, in one embodiment of the present invention, the IV pump unit used for drug delivery is connected not only to a pulse oximeter, but also to other or the same sensors or devices for measuring or monitoring different medical parameters such as the patient's body temperature, heart rhythm, and blood pressure, with such parameters also being used for formulating a schedule of drug administration. In another embodiment of the invention, the IV pump unit integrated with a pulse oximeter is connected to a main controller, wherein the main controller is also connected to one or more medical devices or physiological sensors. In this example, the main controller separately receives data from the IV pump unit and the other medical devices and sensors. The main controller may also be used to control the various functionalities of each of the medical devices or physiological sensors attached to it. In another preferred embodiment, the IV pump unit serves as the main controller for the pulse oximeter and the other one or more medical devices or physiological sensors connected to the IV pump unit. The main controller is preferably a computing device comprising one or more processors, memory, display, interface, software, and operating system that allows control of the one or more medical devices or physiological sensors attached to it. The main controller preferably is also able to receive, process, and store various types of data. Preferably, the main controller is connected to the cloud/internet and one or more databases via a local or remote network (e.g., a LAN or WAN).

Figure 1:
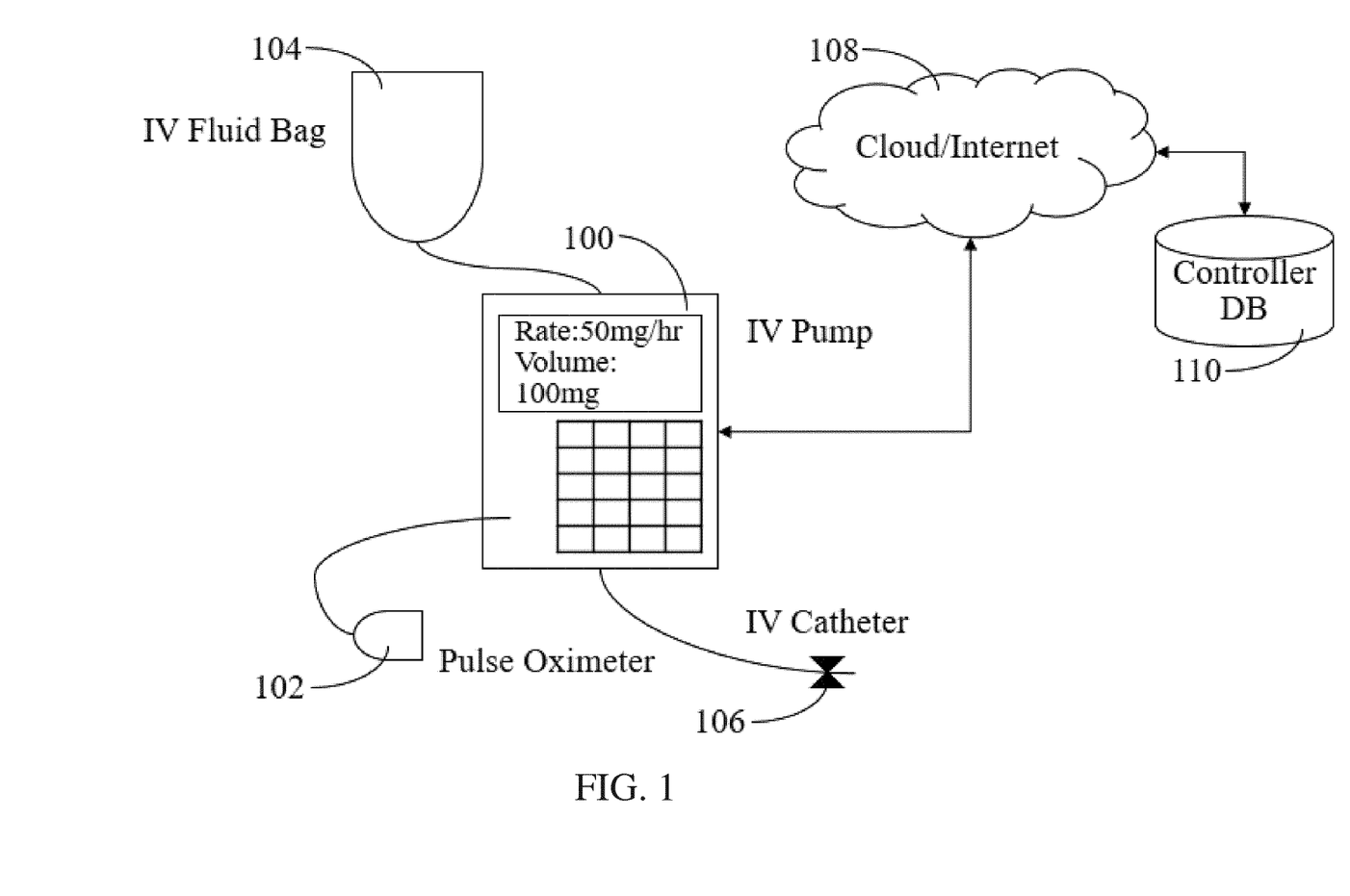
FIG. 1 illustrates a system according to a preferred embodiment of the present invention.

FIG. 1 illustrates a preferred embodiment in accordance with the present invention. An intravenous (IV) pump unit 100, which is connected to a pulse oximeter 102, an intravenous (IV) fluid bag 104, and an IV catheter has access to a controller database 110 via the cloud/internet 108. The IV pump unit 100 uses patient and drug-related information to determine the best schedule of drug delivery for the patient. The patient-related information includes, for example, the patient history, condition, and the drug to be administered. Medical personnel have access to a GUI to allow them to log the effectiveness of the drug. The logged data is used with pulse oximeter data to determine the best schedule of drug delivery for the patient. Preferably, all data inputted into the IV pump unit is saved to the cloud to update the controller database.

Figure 2A:
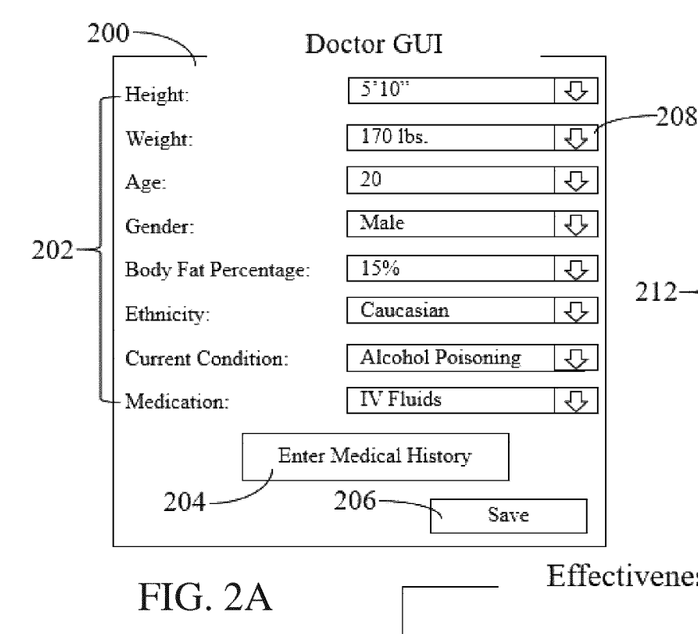
FIGS. 2A-2C illustrate different entry forms displayed on the graphical unit interface of the intravenous pump unit of the present invention.
Figure 2B:
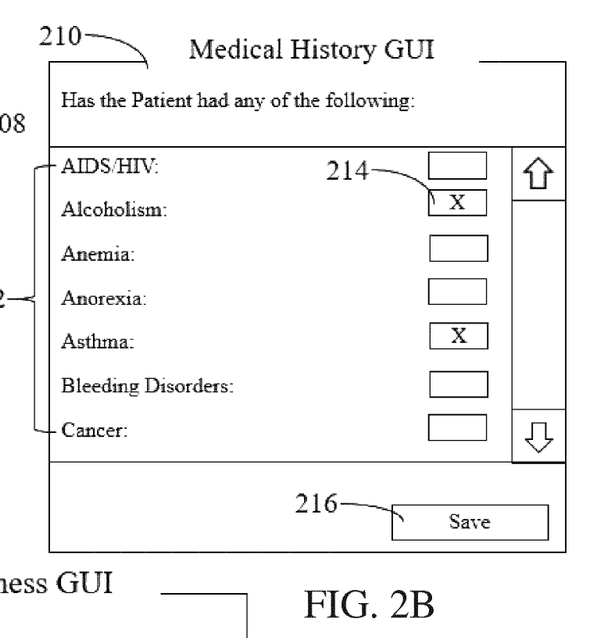
Figure 2C:
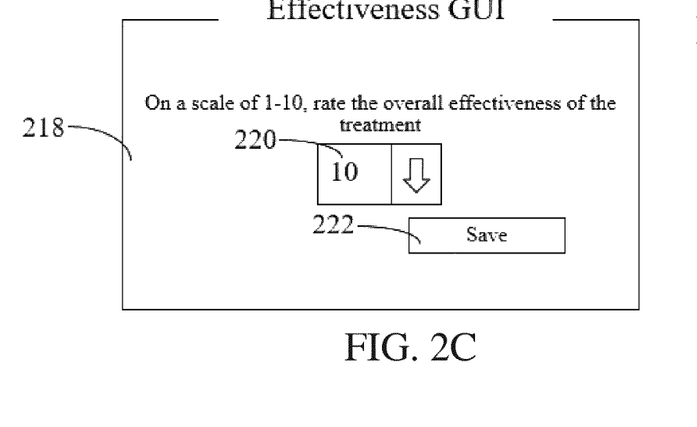

FIGS. 2A-2C illustrate different entry forms displayed on the graphical unit interface of the IV pump unit of the present invention. FIG. 2A shows the doctor GUI form 200 that contain various fields 202 relating to the patient such as height, weight, age, gender, body fat percentage, ethnicity, current condition, and medication. The doctor entry form also includes a button 204 to allow inputting of entries for the various fields and another button 206 for saving entries for the selected fields. FIG. 2A also shows dropdown menu buttons 208 to allow selection of an entry for each of the fields 202. FIG. 2B shows the medical history form 210 that contains different fields 212 corresponding to different diseases or disorders that can be selected by the GUI user by checking the corresponding boxes 214, which in the present case shows that the patient has a history of alcoholism and asthma. As shown, the medical history entry form also has a "Save" button 216 for saving any inputted entries.

FIG. 2C shows the effectiveness entry form 218, which allows the GUI user to enter a value or score between 1-10 by selecting a dropdown button 220. Here, as with the other entry forms, the effectiveness entry form also includes a "Save" button 222. The selected effectiveness value indicates the overall effectiveness of a patient treatment that is measured using various factors. It includes the selected drug delivery schedule as one of the major parameters used in determining treatment effectiveness. The effectiveness rating from 1-10 may be based on a relative scale in which an effectiveness rating of "1" is the lowest or least effective rating while a rating of "10" corresponds to the highest or most effective rating.

In one embodiment, the first time a medical personnel decides on a drug delivery schedule for a patient, the medical personnel will be required by the IV pump unit to enter an initial effectiveness rating. In this case, the medical personnel enters a default value, e.g., "7" as an initial inputted effectiveness rating. Alternatively, the IV pump unit will automatically enter the default value of "7" if the medical personnel opts not to enter any initial effectiveness rating. Upon analysis of collected data during the first day of treatment, a medical personnel updates, if necessary, the effectiveness rating of the previously used drug delivery schedule and either chooses a value higher than or lower than the initially selected "7" effectiveness rating. If, based on the analyzed data from the first day of treatment, the medical personnel decides to update the effectiveness rating to a value higher than the initial rating entered into the IV pump unit, the medical personnel may use the same drug administration schedule for the following day or so. Otherwise, if the analyzed collected data from the first day of treatment is deemed to be not as effective as the medical personnel thought it would be (for example, the patient's condition did not improve after 24 hours, fever did not subside, etc.), the medical personnel will update the effectiveness rating of the previous drug administration schedule by selecting a value lower than the initially selected "7" effectiveness rating, e.g., the medical personnel may decide to update the effectiveness rating by changing the stored value from a "7" down to a "6" or "5." When the medical personnel downgrades the previously used drug delivery schedule for a patient, the medical personnel will preferably also make the necessary changes to the one or more drug delivery schedule parameters that are expected to yield improvements to the patient condition, e.g., increase the frequency of drug delivery, increase the dosage of drug being administered, adjust room temperature, and lower the drug dosage at those times when the patient's pulse rate is the highest.

The effectiveness rating also preferably takes into account scores that may be assigned to one or more medical or physiological parameter depending on their measured values. Thus, the overall score for a selected drug administration schedule may be calculated by determining the individual scores for each measured medical or physiological parameter and then computing their average to obtain the overall score or effectiveness rating. For example, a measured patient body temperature that lies within normal body temperature during the monitoring period after a drug administration may be assigned a score of either "9" or "10." Similarly, a patient's blood pressure that is measured to lie within the normal blood pressure range expected for a patient having a certain weight, age, gender, etc. will likewise be given a score of "9" or "10." The resulting average value of the combined scores is preferably used only as a preliminary effectiveness score that will be presented to a medical personnel who reviews the effectiveness of a selected drug delivery administration. In a preferred embodiment, the medical personnel can manually input an effectiveness rating that is different from the calculated preliminary effectiveness rating. For example, in the case where the calculated effectiveness rating is relatively high because the patient's body temperature and blood pressure are within normal ranges, the medical personnel may downgrade the overall effectiveness score for the selected drug administration schedule if the blood platelet count, for example, is or remains either too high or too low.

Figure 3:
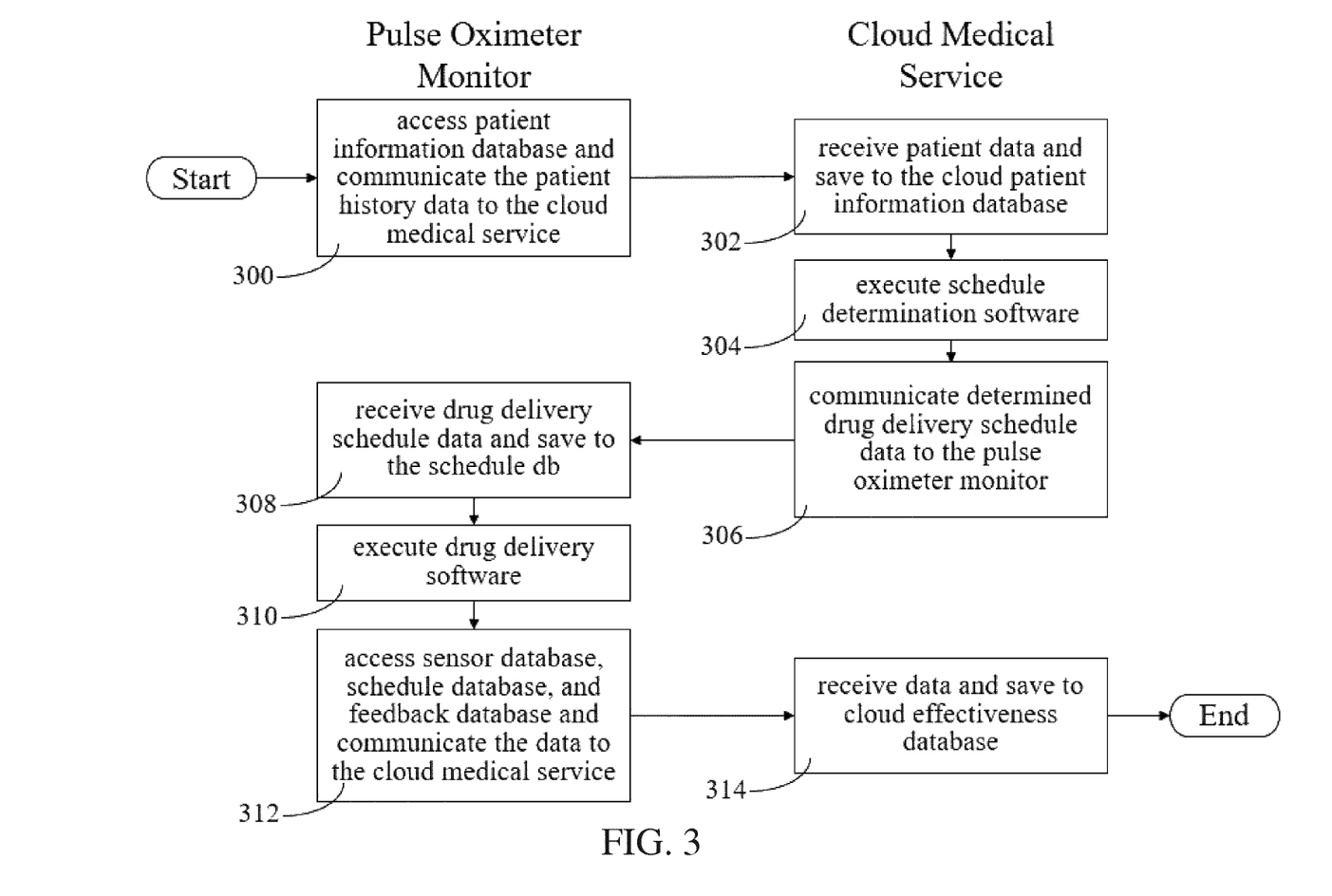
FIG. 3 is a flowchart that illustrates a process according to a preferred embodiment of the present invention.

FIG. 3 shows a process for determining a drug administration schedule for a patient based on pulse oximetry data and patient information. In the first step of the process, the patient information database of the pulse oximeter monitor is accessed, and the patient history data is transmitted by the pulse oximeter monitor to the cloud medical service (step 300). The received patient data is then saved to the cloud patient information database of the cloud medical service (step 302). The schedule determination software is executed (step 304) and the determined drug delivery schedule data is communicated to the pulse oximetry monitor (step 306). The drug delivery schedule data is received and saved to the schedule database (step 308) and the drug delivery software is executed (step 310). The sensor database, schedule database, and feedback database are accessed and data is communicated to the cloud medical service (step 312). Finally, data is received and saved to the cloud effectiveness database (step 314).

Figure 4:
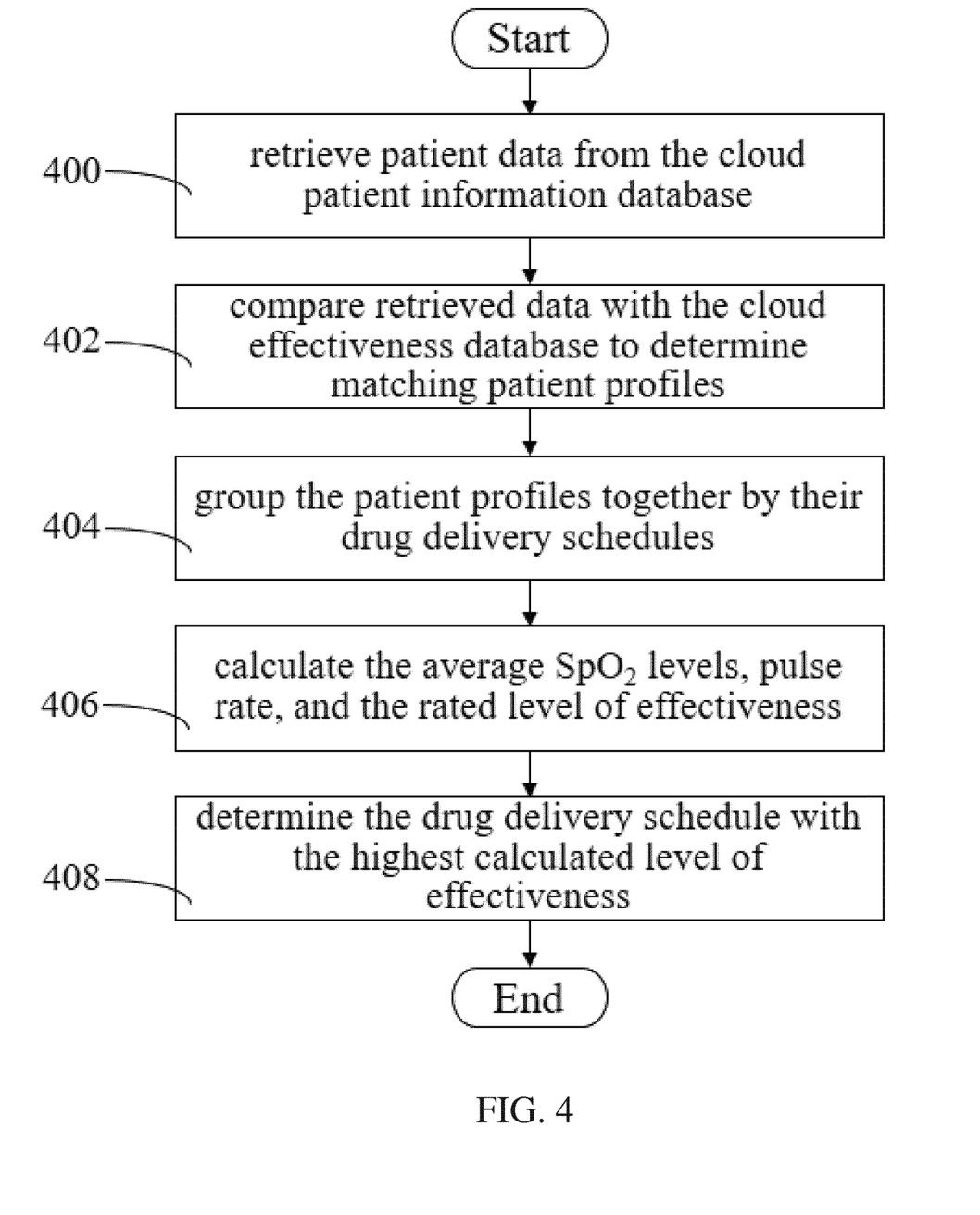
FIG. 4 is a flowchart that illustrates another process according to a preferred embodiment of the present invention.

In FIG. 4, patient data is first retrieved from the cloud patient information database (step 400) and the retrieved data is compared with the cloud effectiveness database to determine matching patient profiles (step 402). The patient profiles are then grouped together according to their drug delivery schedules (step 404). The average SpO2 levels, pulse rate, and the rated level of effectiveness are calculated (step 406), and the drug delivery schedule with the highest calculated level of effectiveness is then determined (step 408).

Figure 5:
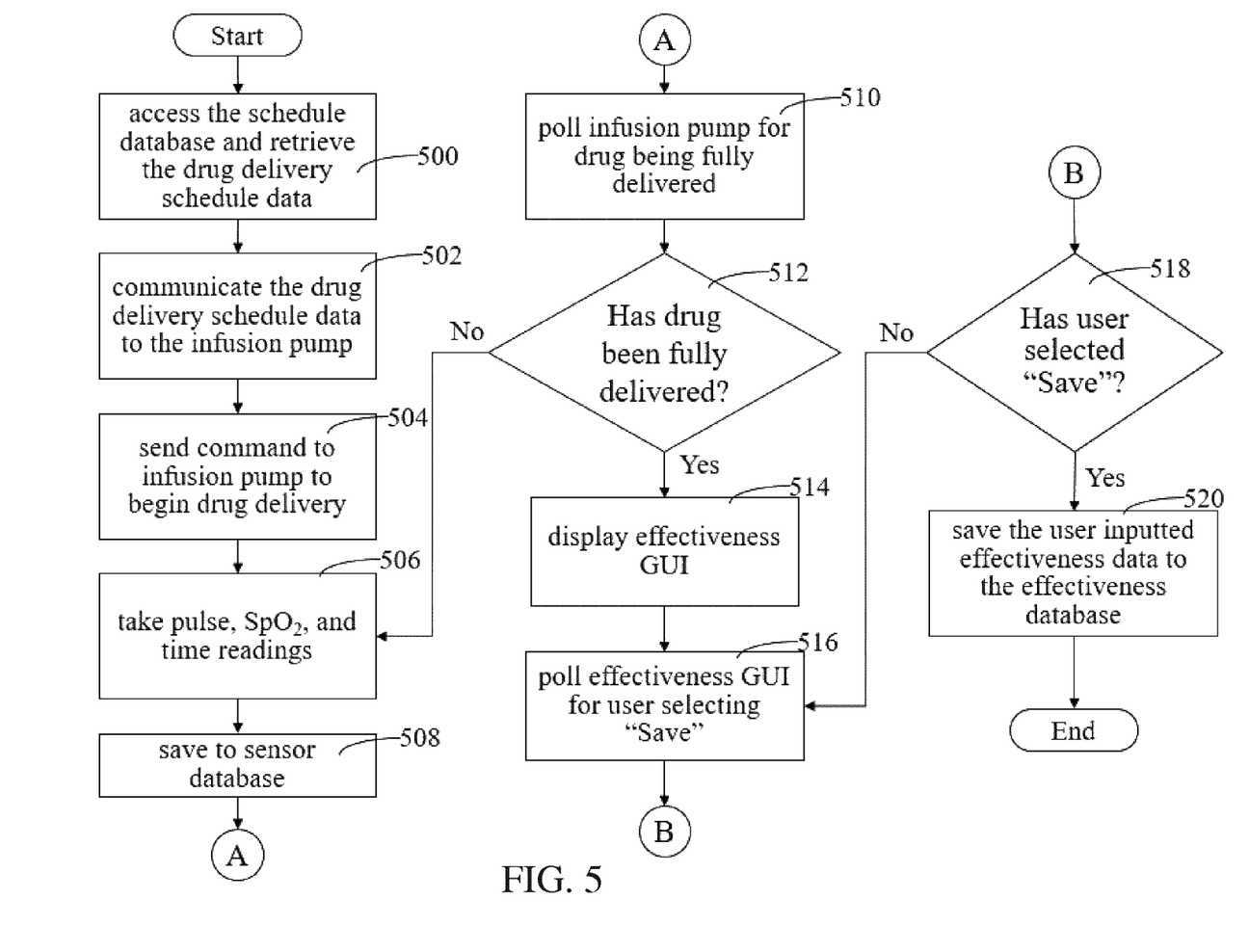
FIG. 5 is a flowchart that illustrates still another process according to a preferred embodiment of the present invention.

In FIG. 5, the schedule database is first accessed and the drug delivery schedule data is retrieved (step 500). The drug delivery schedule data is transmitted to the infusion pump (step 502), and a command is sent to the infusion pump to begin drug delivery (step 504). Pulse rate, SpO2 levels, and time readings are then measured (step 506) and saved to the sensor database (step 508). Then, the infusion pump is polled to determine if the drug administration has been completed (step 510) via the query "Has drug been fully delivered?" (step 512). If not, the process goes back to taking pulse rate, SpO2 level, and time readings (step 506). If the drug has been fully administered, the effectiveness GUI is then displayed (step 514). The effectiveness GUI is polled to determine if the user has selected "Save" (step 516) via the query "Has user selected 'Save'?" (step 518). If the user has not yet selected "Save," the effectiveness GUI is again polled to see if the user has selected to save user-inputted effectiveness data (step 516). If so, the user inputted effectiveness data is saved to the effectiveness database (step 520).

In one embodiment of the invention, a physician retrieves, via an IV pump unit's GUI, a patient's history, patient condition, and preliminary diagnosis based on observed symptoms and results of earlier tests and examinations. Additional tests and a second opinion from at least one specialist confirms that the patient has breast cancer and is also suffering from hypertension and elevated cholesterol level. The physician also retrieves and reviews the prescribed treatment protocol, which includes a combination of drugs and radiation treatment to treat the breast cancer, a beta-blocker to treat hypertension, and a statin to lower the patient's cholesterol level. Based on the patient's current medical condition, it was decided to perform controlled drug administration via the IV pump unit. Based on the known optimal drug delivery timing for the anti-cancer, beta-blocker, and statin drugs, the physician decides on an initial drug delivery schedule for the three drug classes, and also schedules SpO2 level and pulse rate data acquisition and monitoring using a pulse oximeter connected to the IV pump unit. The physician then enters the prescribed schedule of drug delivery for the patient for the first 24-hours, and also prescribes the monitoring of SpO2 level, pulse rate, and other patient physiological parameters that include blood pressure, body temperature, and heart's electrical activity.

The physician enters an initial effectiveness rating of "7" for the selected drug delivery protocol into the IV pump unit via the interface and schedules a review of the whole procedure after a 24-hour period. The various medical parameters that include the SpO2 level, pulse rate, blood pressure, body temperature, and electrical activity of the heart are monitored over a 24-hour period. Data from the measured medical parameters are transmitted to the IV pump unit and temporarily stored in its memory. The stored data are subsequently transmitted for storage to a hospital's network server. The following day, the physician uses the IV pump unit to display the acquired medical parameter data and analyzes them using the data processing software for each set of acquired data. From the various sets of acquired data relating to the SpO2 level, pulse rate, blood pressure, body temperature, and heart electrical activity over the last 24-hours, the IV pump unit displays a calculated effectiveness rating of "7." After performing data correlation for the various acquired data sets, reviewing the patient's current medical condition and history, and taking into account the patient's age, weight, and known sensitivity to at least one of the administered drugs, the physician concludes that the patient's medical condition did not show any signs of improvement relative to the patient's condition during the last 24 hours or so. The physician thus updates the effectiveness rating of the previous drug delivery schedule by lowering the initial score of "7" to "6." This information is then transmitted and stored into the IV pump unit's memory, and later on, to one of the hospital's network servers.

After analyzing the newly-acquired data and information, the physician also accesses and reviews, via the IV pump unit, previously-used drug delivery schedules for other past patients with profiles similar to the patient being treated and determines which of the similar previously-used treatment schedule protocols has the highest effectiveness rating. The physician then decides to make changes to the drug delivery schedule for the next 24-hours based on the newly-acquired medical parameter data and stored drug delivery schedules previously used for patients with similar profiles as the present patient. In this case, the physician changes the set time for the administration of one of the drugs. The physician follows the same procedure on the third day of the treatment protocol, but this time changes the delivery rate for one of the drugs and reduces the frequency of drug delivery for the other drugs from three to two over the next 24-hour period.

The physician continues to make adjustments to the drug delivery schedule until a particular drug administration schedule appears to reach an optimal level based on the observed patient's response to the tweaks made to the drug delivery schedule during the treatment period. The patient's medical records are then updated via the IV pump unit by appending the medical personnel's diagnosis, the effectiveness ratings for the one or more drug delivery schedules used in the treatment protocol, recommendations and comments, and schedule of the next medical personnel patient visitations in the patient's records stored in the patients database. The medical personnel preferably also inputs the schedule for the follow-up patient visit with an assigned medical personnel.

In a preferred embodiment of the invention, a medical personnel attempting to access data or information using the IV pump unit is required to undergo an authentication process. Authentication may be performed via one or more authentication methods that includes entry of password, digital or script signature, facial or voice recognition, fingerprint scanning, retinal scanning, or iris recognition. In this case, the IV pump unit compares the received medical personnel's voice data with the medical personnel's registered voice data previously stored in the medical personnel database to determine if the medical personnel is authorized to access the measured patient health data, decoded data, or correlated data. If the medical personnel is authorized, the IV pump unit displays data that includes, for example, the correlation between the decoded data and the corresponding patient data previously stored in one or more databases.

In the case where the medical personnel is not recognized by the IV pump unit via an authentication procedure such as through voice or facial recognition, the acquired health-related data is preferably not stored by the IV pump unit and the current health-related data of the patient is also preferably not uploaded to the one or more hospital databases. The IV pump unit then preferably provides an alert notifying one or more medical personnel that the person presently attempting to access the patient data does not belong to the list of individuals authorized to monitor and treat the patient and also to access the patient's medical and personal data. The alert provided by the IV pump unit may also be in the form of an auditory alert directed to the person trying to access the patient data, as well as to the patient inside the room.

The hospital network may be a local or remote network that can be used for transmitting and storing patient data in its one or more databases. Patient data preferably include name, age, address, gender, patient room assignments, patient medical history, diagnosis, treatment plans, prescribed medication, known allergies, family history, and other relevant information relating to the patient. The hospital network also preferably stores medical personnel data in the medical personnel database. Medical personnel data include a list of registered medical personnel such as authorized physicians, medical residents, interns, clerks, nurses, nursing aides, laboratory technicians, radiology technicians, and other healthcare professionals involved in patient care and treatment. Medical personnel data also preferably include voice data such as a medical personnel's voice signature, speech patterns, known voice input answers, specific phrases, and other voice data relating to an audio or voice input. Preferably, the system uses the medical personnel's voice data to, among others, identify and authenticate the medical personnel designated to monitor, diagnose or treat a patient. Furthermore, medical personnel data also preferably includes information about the medical personnel's field of expertise, names of patients admitted under each physician, authorized nurses for each room, department, or floor within the health facility, and data relating to the medical personnel's authorization level and access privileges for accessing patient or medical personnel information or data.

In accordance with the various aspects of the present invention, various medical apparatuses and persons may be detected and identified according to the various embodiments of the present invention using, for example, pattern recognition, image recognition, image registration, object recognition, facial recognition, feature extraction, color recognition, optical character recognition, motion analysis covering tasks such as egomotion, tracking, and optical flow, pose estimation, machine vision, machine learning, content-based image retrieval, shape recognition, artificial intelligence, neural networks, and other methods of image processing as well as other types of computer vision-based technology.

In accordance with the various aspects of the present invention, various audio signals and persons are detected and identified according to the various embodiments of the present invention using, for example, speech recognition, speech analysis, audio registration, audio extraction, and other methods of audio processing as well as other types of computer aid-based technology. The audio device used according to the various embodiments of the invention may also accept vital sign parameters communicated to the patient as a data entry which allows the IV pump unit to process natural language.

In accordance with the various aspects of the present invention, processor comprises data processors, image processors, central processing unit, or any variety of multi-core processing device.

The communications module is a device or a component of a device that allows communication—e.g., sending and receiving of commands, triggers, notifications, prompts, acknowledgments, information, messages, forms, and various types of data—between the image monitoring device and the computing device, and the alarm system.

The present invention is not intended to be restricted to the several exemplary embodiments of the invention described above. Other variations that may be envisioned by those skilled in the art are intended to fall within the disclosure.

The invention claimed is:

1. A method of scheduling drug administration using a pulse-oximetry integrated intravenous fluid system, the method comprising:
    retrieving patient data from at least one database over a communication network, the patient data comprising patient history, patient condition, diagnosis, and information relating to one or more drugs to be administered to a patient;
    displaying the retrieved patient data on a screen of an intravenous pump unit interface;
    monitoring pulse oximetry data from the patient via a pulse oximeter;
    formulating a schedule of drug administration based on the pulse oximetry data, patient history, patient condition, diagnosis, and information relating to the one or more drugs;
    monitoring one or more effects of the one or more drugs administered to the patient via the intravenous pump unit;
    calculating an effectiveness rating for the set drug administration schedule based on the monitored effects, the effectiveness rating indicating the efficacy of the one or more administered drugs and/or extent of improvement in the patient's medical condition by the drug administration;
    displaying a user interface allowing a user to update the calculated effectiveness rating; and
    updating a patient record for the patient stored in the at least one database based on the monitored effects and calculated or updated effectiveness rating.

2. The method of claim 1, wherein formulating the schedule of drug administration comprises selecting a drug administration schedule from a plurality of drug administration schedules.

3. The method of claim 2, wherein selecting the drug administration schedule is based on drug administration schedules previously used for patients with similar medical profiles.

4. The method of claim 1, wherein the one or more drugs are associated with at least one genetic factor.

5. The method of claim 4, wherein the genetic factor includes a circadian gene.

6. The method of claim 1, further comprising modifying the set drug administration schedule based on at least one of the pulse oximetry data, one or more observed patient responses to the set drug administration schedule, the calculated effectiveness rating, and an effectiveness rating inputted by a medical personnel.

7. The method of claim 1, wherein the intravenous pump unit can control one or more drug delivery rates, at least one environment parameter, dosing frequency, and amount of drug delivered over the duration of the treatment period.

8. A system of scheduling drug administration using a pulse-oximetry integrated intravenous fluid system, the system comprising:
    at least one database that stores patient data comprising patient history, patient condition, diagnosis, and information relating to one or more drugs to be administered to a patient;
    an intravenous pump unit interface that displays the retrieved patient data on a screen;
    a pulse oximeter that monitors pulse oximetry data from the patient;
    a processor that executes instructions stored in memory, wherein execution of the instructions by the processor:
        formulates a schedule of drug administration based on the pulse oximetry data, patient history, patient condition, diagnosis, and information relating to the one or more drugs, wherein an intravenous pump unit monitors one or more effects of the one or more drugs administered to the patient,
        calculates an effectiveness rating for the set drug administration schedule based on the monitored effects, the effectiveness rating indicating the efficacy of the one or more administered drugs and/or extent of improvement in the patient's medical condition by the drug administration;
        causes display of a user interface allowing a user to update the calculated effectiveness rating; and
        updates a patient record for the patient stored in the at least one database based on the monitored effects and calculated or updated effectiveness rating.

9. The system of claim 8, wherein the processor formulates the schedule of drug administration by selecting a drug administration schedule from a plurality of drug administration schedules.

10. The system of claim 9, wherein the processor selects the drug administration schedule based on drug administration schedules previously used for patients with similar medical profiles.

11. The system of claim 8, wherein the one or more drugs are associated with at least one genetic factor.

12. The system of claim 11, wherein the genetic factor includes a circadian gene.

13. The system of claim 8, wherein the processor executes further instructions to modify the set drug administration schedule based on at least one of the pulse oximetry data, one or more observed patient responses to the set drug administration schedule, the calculated effectiveness rating, and an effectiveness rating inputted by a medical personnel.

14. The system of claim 8, wherein the intravenous pump unit can control one or more drug delivery rates, at least one environment parameter, dosing frequency, and amount of drug delivered over the duration of the treatment period.

15. A non-transitory computer-readable storage medium, having embodied thereon a program executable by a processor to perform the method of claim 1.

* * * * *